United States Patent [19]

Nemoto et al.

[11] Patent Number: 4,836,957
[45] Date of Patent: Jun. 6, 1989

[54] STABILIZED ACTIVE FORMS OF VITAMIN $D_3$

[75] Inventors: Kaoru Nemoto; Kazuo Igusa; Toshichika Ogasawara, all of Tokyo, Japan

[73] Assignee: Chugai Seiyaku Kabushiki Kaisha, Tokyo, Japan

[21] Appl. No.: 828,596

[22] Filed: Feb. 11, 1986

[30] Foreign Application Priority Data

Feb. 14, 1985 [JP] Japan .................. 60-28073

[51] Int. Cl.$^4$ ............................................. C07J 9/00
[52] U.S. Cl. ................................ 260/397.2; 514/196
[58] Field of Search ...................................... 260/397.2

[56] References Cited

U.S. PATENT DOCUMENTS 4,164,569  8/1979  Ikushima et al. ................ 424/174

FOREIGN PATENT DOCUMENTS

| | | | |
|---|---|---|---|
| 0132821 | 2/1985 | European Pat. Off. | 260/397.2 |
| 0144434 | 6/1985 | European Pat. Off. | 260/397.2 |
| 51-128417 | 11/1976 | Japan | 260/397.2 |
| 53-136512 | 11/1978 | Japan | 260/397.2 |
| 55-069562 | 4/1980 | Japan | 260/397.2 |
| 304182 | 12/1954 | Switzerland . | |
| 799068 | 7/1958 | United Kingdom | 260/397.2 |
| 2052976 | 2/1981 | United Kingdom | 260/397.2 |

OTHER PUBLICATIONS

Merck Index, Tenth Ed., (1983), pp. 4359 and 8949.
Organic Chemistry, Fourth Ed., (1983), pp. 923–925.

*Primary Examiner*—Werren B. Lone
*Attorney, Agent, or Firm*—Browdy and Neimark

[57] ABSTRACT

A preparation containing an active form of vitamin $D_3$ which is stabilized by incorporation of an amino acid that is neither one containing a sulfur atom or an acid amino group in its structure, nor an acidic amino acid, nor a salt of a basic amino acid is disclosed. Examples of said amino acids that may be used as stabilizers of the active form of vitamin $D_3$ include neutral amino acids such as alanine, valine, proline, phenylalanine, tryptophan, leucine, isoleucine, glycine and serine, and basic amino acids such as lysine, arginine and histidine.

3 Claims, No Drawings

STABILIZED ACTIVE FORMS OF VITAMIN $D_3$

BACKGROUND OF THE INVENTION

The present invention relates to stabilized preparations of active forms of vitamin $D_3$.

Active derivatives of vitamin $D_3$ represented by $1\alpha,25$-dihydroxyvitamin $D_3$ and $1\alpha$-hydroxyvitamin $D_3$ have the ability to improve calcium metabolism, especially bone metabolism, and find extensive clinical use not only in patients under blood dialysis therapy who suffer from bone diseases resulting from impaired vitamin D activity in kidneys but also in the treatment of diseases that are difficult to cure by conventional vitamin $D_3$ drugs, such as chronic renal insufficiency, hypoparathyroidism, vitamin D-resistant rickets and osteomalacia. These active forms of vitamin $D_3$ are also administered to premature babies to sustain their growth.

The active forms of vitamin $D_3$ have such strong physiological activities that their single doses are limited to very small amounts. In order to ensure uniformity in their levels in preparations and their stability as well, the active forms of vitamin $D_3$ are most often administered in the form of soft capsules filled with oily solutions such as middle-chain aliphatic acid triglycerides, or in the form of oily liquids.

Practicing doctors who are attending patients with chronic renal insufficiency see the strong need to develop injections of active forms of vitamin $D_3$ that can be directly administered into the patient's blood during blood dialysis. Active forms of vitamin $D_3$ administered in the form of oily liquids to premature babies and infants have the unpleasant taste of oils and cases have been reported that infants to whom the oily liquids had been repeatedly administered eventually refused to take further doses of the liquids. Oily liquids of active forms of vitamin $D_3$ may be administered to infants in the form of mixtures with milk or fruit juice, but the oily liquids will not mix uniformly with milk or fruit juice and present considerable difficulty in maintaining the exact amount of dose since the formulation will partly stick to the inner surface of nursing bottles or cups. Stability test with active forms of vitamin $D_3$, which are fat-soluble vitamins, after they were solubilized with a variety of solubilizers to form liquid preparations or made into tablets or fine particles with the aid of various excipients showed that these preparations were unable to remain stable and degraded quickly at room temperature.

SUMMARY OF THE INVENTION

The present inventors therefore made concerted efforts to develop preparations containing active forms of vitamin $D_3$ that will remain stable for a long time. As a result, the present inventors found that the stability of the active forms of vitamin $D_3$ is markedly improved by incorporation of neutral or basic amino acids. Upon further research, it was unexpectedly found that the most effective amino acid is a neutral or basic amino acid having no sulfur atom or acid amide group ($—CONH_2$) in its structure but that basic amino acids in salt forms and acidic amino acids are deleterious to the stability of active forms of vitamin $D_3$.

The present invention has been accomplished on the basis of these new findings relates to a preparation of active form of vitamin $D_3$ that is stabilized by the addition of a neutral or basic amino acid containing no sulfur atom or acid amide group.

DETAILED DESCRIPTION OF THE INVENTION

Illustrative active forms of vitamin $D_3$ that are stabilized by the present invention include vitamin $D_3$ compounds having a hydroxyl group at $1\alpha$-position such as $1\alpha$-hydroxyvitamin $D_3$, $1\alpha,24$-dihydroxyvitamin $D_3$, $1\alpha,25$-dihydroxyvitamin $D_3$, $1\alpha,24,25$-trihydroxyvitamin $D_3$ and $26,27$-hexafluoro-$1\alpha,25$-dihydroxyvitamin $D_3$, as well as those which contain no $1\alpha$-hydroxyl group such as $24$-hydroxyvitamin $D_3$ and $25$-hydroxyvitamin $D_3$.

Illustrative amino acids that may be used as stabilizers in the present invention include neutral amino acids such as alanine, valine, proline, phenylalanine, tryptophan, leucine, isoleucine, glycine and serine, and basic amino acids such as lysine, arginine and histidine. The desired stabilizing effects are also exhibited by substances that have these amino acid portions in their structures and examples of such substances are N-glycylglycine having the glycine portion, and glycylalanine having the alanine portion.

In the practice of the present invention, the amount of the amino acid added to a specific active form of vitamin $D_3$ is in no way limited to any particular value and the amino acid may be used in any amount that will exhibit the intended effect upon incorporation into the active form of vitamin $D_3$. Usually, the amino acid is added in an amount ranging from 1 to 100,000 times the weight of the active form of vitamin $D_3$. In case of a liquid preparation, the amino acid is preferably used in an amount 10 - 500 times the weight of the active form of vitamin $D_3$; in case of a solid preparation, a preferred amount ranges from 5,000 to 50,000 times the weight of the active form of vitamin $D_3$. Two or more of the amino acids defined above may be employed.

In order to make a liquid preparation in accordance with the present invention using an aqueous medium, the active form of vitamin $D_3$ is solubilized with a nonionic surfactant and the stabilizer amino acid is then dissolved in the solution. If desired, pharmaceutically acceptable additives that will not adversely affect the stability of the active form of vitamin $D_3$ may be added, and they include, for example, isotonizers, buffers, flavorings, preservatives, pH modifiers and thickeners; the so prepared mixture may then be worked up into injections, syrups, emulsions or cream by routine procedures.

The concept of the present invention is also applicable to the making of solid preparations; in this case, the active form of vitamin $D_3$ is rendered compatible with the stabilizer amino acid most preferably by dispersing a predetermined amount of the amino acid directly in an alcoholic solution or an oily solution of the active form of vitamin $D_3$. The resulting mixture of the active form of vitamin $D_3$ and the amino acid may then be blended with an excipient, binder, disintegrator, lubricant, ointment base or a suppository base, followed by working up into tablets, granules, powders, capsules, ointments or suppositories in accordance with the usual practice.

The so obtained preparation of an active form of vitamin $D_3$ exhibits excellent stability with time, as will be described in greater detail by the following examples which are in no way intended as limiting the scope of the present invention.

EXAMPLE 1

In 1 ml of an alcoholic solution containing 200 μg/ml of 1α-hydroxyvitamin $D_3$, 20 mg of polyoxyethylene (60 mole) hydrogenated castor oil derivative (Nikkol HCO-60) was dissolved. After addition of 40 mg of stabilizer arginine and 10 g of glucose (isotonizer), the mixture was diluted in distilled water for injection to make a total of 200 ml. The solution was passed through a membrane filter and charged into nitrogen-purged ampules in 2-ml portions. The ampules were fused and sterilized at 110° c. for 30 minutes, thereby preparing injections each containing 2 μg of 1α-hydroxyvitamin $D_3$ in one ampule.

Stabilizer-free samples were prepared by repeating the same procedures and compared with the samples of the present invention for the stability of 1α-hydroxyvitamin $D_3$ by determining its quantities by HPLC both immediately after the preparation and after acceleration testing. The results are shown in Table 1, wherein each of the figures represents the percentage of residual 1α-hydroxyvitamin $D_3$ as a relative value with the level for the unsterilized sample being taken as 100.

TABLE 1

| Stabilizer | After sterilization | After acceleration testing (50° C. × 15 days) |
| --- | --- | --- |
| positive | 98.6 | 94.5 |
| negative | 67.8 | 10.9 |

EXAMPLE 2

In 2 ml of an alcoholic solution containing 100 μg/ml of 1α,25-dihydroxyvitamin $D_3$, 60 mg of polyoxyethylene (50 mole) hydrogenated castor oill derivative (Nikkol HCO-50) was dissolved. After addition of 60 mg of stabilizer proline, the mixture was diluted in purified water to make a total of 400 ml. The solution was charged into glass vials in 20-ml portions. The vials were purged with argon gas and stoppered to make solutions each containing 0.5 μg/ml of 1α,25-dihydroxyvitamin $D_3$. A stabilizer-free sample was prepared as in Example 1. The results of a stabilizer test conducted with the two kinds of samples are shown in Table 2, wherein each of the figures represents the percentage of residual 1α,25-dihyroxyvitamin $D_3$ as a relative value with the level for the solution just after preparation being taken as 100.

TABLE 2

| Stabilizer | After acceleration testing (40° C. × 60 days) |
| --- | --- |
| positive | 97.9 |
| negative | 24.3 |

EXAMPLE 3

In 5 ml of an alcoholic solution containing 100 μg of 26,27-hexafluoro-1α,25-dihydroxyvitamin $D_3$, 50 mg of poyoxyethylene (100 mole) hydrogenated caster oil derivative (Nikkol HCO-100) was dissolved. After addition of 100 mg of stabilizer alanine and 70 g of refined sucrose (sweetener), the mixture was diluted in purified water to make a total of 1,000 ml. The solution was charged into glass vials in 20-ml portions. The vials were purged with nitrogen gas and stoppered to make syrups each containing 0.5 μg/ml of 26,27-hexafluoro-1α,25-dihydroxyvitamin $D_3$. A stabilizer-free sample was prepared as in Example 1. The results of a stability test conducted with the two kinds of samples are shown in Table 3, wherein each of the figures represents the percentage of residual 26,27-hexafluoro-1α,25-dihydroxyvitamin $D_3$ as a relative value with the level for the sample just after preparation being taken as 100.

TABLE 3

| Stabilizer | After acceleration testing (50° C. × 20 days) |
| --- | --- |
| positive | 97.7 |
| negative | 31.2 |

EXAMPLE 4

In an alcoholic solution containing 200 μg of 24-hydroxyvitamin $D_3$, 20 mg of polyoxyethylene (60 mole) hydrogenated castor oil derivative (Nikkol HCO-60) was dissolved. After addition of 40 mg of stabilizer valine, the mixture was diluted in distilled water to make a total of 200 ml. The solution was charged into glass vials in 20-ml portions. The vials were purged with argon gas and stoppered to make solutions each containing 1 μg/ml of 24-hydroxyvitamin $D_3$. A stabilizer-free sample was prepared as in Example 1. The results of a stability test conducted with the two kinds of samples are shown in Table 4, wherein each of the figures represents the percentage of residual 24-hydroxyvitamin $D_3$ as a relative value with the level for the sample just after preparation being taken as 100.

TABLE 4

| Stabilizer | After acceleration testing (40° C. × 60 days) |
| --- | --- |
| positive | 96.2 |
| negative | 22.3 |

EXAMPLE 5

To 200 g of glycine, 50 ml of an alcoholic solution containing 2 μg of 1α-hydroxyvitamin $D_3$, was slowly added under agitation. Alcohol was evaporated from the intimate mixture, thereby producing a powder containing 0.5 μg/ml of 1α-hydroxyvitamin $D_3$. A control sample was prepared as above except that glycine was replaced by lactose. The results of a stability test conducted with the two powders are shown in Table 5, wherein each of the figures represents the percentage of residual 1α-hydroxyvitamin $D_3$ as a relative value with the level for the powder just after preparation being taken as 100.

TABLE 5

| Stabilizer | After acceleration testing (40° C. × 20 days) |
| --- | --- |
| positive | 94.8 |
| negative | 7.3 |

EXAMPLE 6

Histidine (150 g) was intimately mixed with 10 g of a middle-chain aliphatic acid triglyceride solution containing 500 μg/ml of 1α,25-dihydroxyvitamin $D_3$. The slurry was mixed with 287.5 g of anhydrous lactose (excipient) and 2.5 g of magnesium stearate (lubricant). Using a die (6 mmφ,) tablets each weighing 90 mg and containing 1 μg of 1α,25-dihydroxyvitamin $D_3$ were prepared. Control tablets were prepared as above except that histidine was replaced by anhydrous lactose. The results of a stability test conducted with the two powders are shown in Table 6, wherein each of the figures represents the percentage of residual $1\alpha,25$-dihydroxyvitamin $D_3$ as a relative value with the level for the powder just after preparation being taken as 100.

TABLE 6

| Stabilizer | After acceleration testing (50° C. × 20 days) |
|---|---|
| positive | 95.8 |
| negative | 16.3 |

EXAMPLE 7

Phenylalanine (20 g) was mixed under warming with 150 g of polyoxyethylene monostearate containing 10 μg/g of $1\alpha,24,25$-trihydroxyvitamin $D_3$. To the mixture, 330 g of macrogol ointment (Japanese Pharmacopoeia) was added in small portions to provide a homogeneous texture, thereby making an ointment containing 3 μg/g of $1\alpha,24,25$-trihydroxyvitamin $D_3$. A stabilizer-free sample was prepared as above except that phenylalanine was replaced by mannitol. The results of a stability test conducted with the two kinds of samples are shown in Table 7, wherein each of the figures represents the percentage of residual $1\alpha,24,25$-trihydroxyvitamin $D_3$ as a relative value with the level for the ointment just after preparation being taken as 100.

TABLE 7

| Stabilizer | After acceleration testing (40° C. × 60 days) |
|---|---|
| positive | 93.7 |

TABLE 7-continued

| Stabilizer | After acceleration testing (40° C. × 60 days) |
|---|---|
| negative | 20.9 |

We claim:
1. A preparation comprising:
an active form of vitamin $D_3$ selected from the group consisting of 1 alpha-hydroxyvitamin $D_3$, 1 alpha,24-dihydroxyvitamin $D_3$, 1 alpha,25-dihydroxyvitamin $D_3$; 1 alpha, 24, 25-trihydroxyvitamin $D_3$; 26,27-hexafluoro-1alpha, 25-dihydroxyvitamin $D_3$, 24-hydroxy-vitamin $D_3$; and 25-hydroxyvitamin $D_3$ and a stabilizing amount of a basic or neutral amino acid, wherein said preparation is free of acidic amino acids and salts of basic amino acids, and wherein said amino acid is free of acid amide groups and sulfur-atoms.

2. A preparation according to claim 1 wherein said amino acid is at least one member selected from the group consisting of alanine, valine, proline, phenylalanine, tryptophan, leucine, isoleucine, glycine, serine, lysine, arginine and histidine.

3. A preparation comprising an active form of vitamin $D_3$ selected from the group consisting of 1 alpha-hydroxyvitamin $D_3$; 1 alpha,24-dihydroxyvitamin $D_3$; 1 alpha,25-dihydroxyvitamin $D_3$; 1 alpha, 24,25-trihydroxyvitamin $D_3$; 26,27-hexafluoro-1 alpha, 25-dihydroxyvitamin $D_3$, 24-hydroxy-vitamin $D_3$; and 25-hydroxyvitamin $D_3$ and a stabilizing amount of an amino acid selected from the group consisting of alanine, valine, proline, phenylalanine, tryptophan, leucine, isoleucine, glycine, serine, lysine, arginine and histidine, salts thereof, and N-glycyl derivatives thereof, wherein said preparation is free of acidic amino acids and salts of basic amino acids.

* * * * *